(12) United States Patent
Shigeno et al.

(10) Patent No.: US 7,709,181 B2
(45) Date of Patent: May 4, 2010

(54) CYANINE COMPOUND AND OPTICAL RECORDING MATERIALS

(75) Inventors: Koichi Shigeno, Tokyo (JP); Toru Yano, Tokyo (JP)

(73) Assignee: Adeka Corporation, Tokyo (JP)

( * ) Notice: Subject to any disclaimer, the term of this patent is extended or adjusted under 35 U.S.C. 154(b) by 361 days.

(21) Appl. No.: 11/664,607

(22) PCT Filed: Sep. 21, 2005

(86) PCT No.: PCT/JP2005/017375

§ 371 (c)(1),
(2), (4) Date: Apr. 4, 2007

(87) PCT Pub. No.: WO2006/038464

PCT Pub. Date: Apr. 13, 2006

(65) Prior Publication Data

US 2007/0259294 A1    Nov. 8, 2007

(30) Foreign Application Priority Data

Oct. 7, 2004   (JP)   ............................. 2004-295111

(51) Int. Cl.
G11B 7/24   (2006.01)
(52) U.S. Cl. ................. 430/270.21; 430/945; 428/64.4; 428/64.8; 369/284
(58) Field of Classification Search ........................ None
See application file for complete search history.

(56) References Cited

U.S. PATENT DOCUMENTS 3,577,238 A    5/1971   Rochester (Continued)

FOREIGN PATENT DOCUMENTS

JP    61-126555    6/1986

(Continued)

OTHER PUBLICATIONS

Machine translation of JP 2003-171571.*

(Continued)

*Primary Examiner*—Martin J Angebranndt
(74) *Attorney, Agent, or Firm*—Young & Thompson

(57) ABSTRACT

Cyanine compounds represented by the general formula (I) which exhibit decomposition behavior suitable for the optical recording material to be used in optical recording layers of optical recording media for high-speed recording: (I) wherein A and B are each an optionally substituted benzene or naphthalene ring; X is O, S, Se, $CR^3R^4$, or NY; at least either of $R^1$ and $R^2$ is a group represented by the general formula (II) or (III) and when only either is a group represented thereby, the other is an organic group having 1 to 30 carbon atoms; $R^3$ and $R^4$ are each an organic group having 1 to 30 carbon atoms; Y is hydrogen or an organic group having 1 to 30 carbon atoms; at least either of $Y^1$ and $Y^2$ is a group represented by the general formula (IV) and when only either is a group represented thereby, the other is hydrogen or an organic group having 1 to 30 carbon atoms; Z is hydrogen, halogeno, or cyano; $An^{m-}$ is an m-valent anion; m is an integer of 1 or 2; and p is a coefficient capable of keeping the electric charge neutral.

11 Claims, 1 Drawing Sheet

U.S. PATENT DOCUMENTS

| | | | |
|---|---|---|---|
| 7,425,401 B2* | 9/2008 | Yano et al. | 430/270.21 |
| 2005/0031993 A1* | 2/2005 | Yano et al. | 430/270.21 |
| 2005/0094548 A1* | 5/2005 | Wada et al. | 369/275.4 |
| 2006/0286483 A1* | 12/2006 | Yano et al. | 430/270.21 |
| 2008/0033179 A1* | 2/2008 | Yano et al. | 546/277.4 |

FOREIGN PATENT DOCUMENTS

| | | |
|---|---|---|
| JP | 2001-047740 | 2/2001 |
| JP | 2003-171571 | 6/2003 |
| JP | 2003-231359 | 8/2003 |
| JP | 2004-195765 | 7/2004 |

OTHER PUBLICATIONS

Machine translation of JP 2003-231359.*
Machine translation of JP 2004-195765.*
European Patent Office issued a European Search Report dated May 8, 2009, Application No. 05 78 5728.

* cited by examiner

[Figure 1]
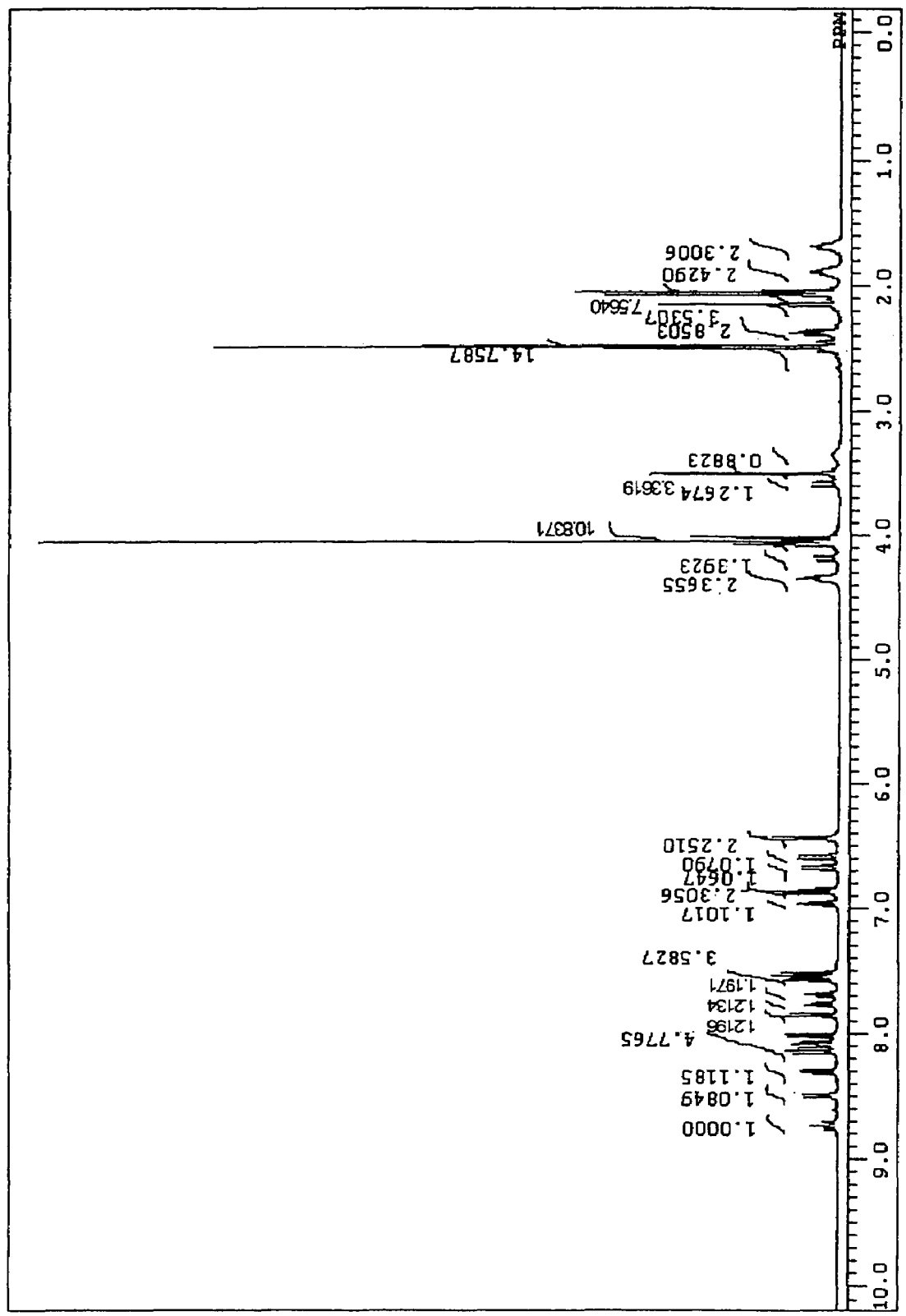

CYANINE COMPOUND AND OPTICAL RECORDING MATERIALS

TECHNICAL FIELD

The present invention relates to a novel cyanine compound and an optical recoding material comprising the cyanine compound. The cyanine compound is suitable for an optical recording material and also useful as a light absorbing material for an optical filter in an image display device.

BACKGROUND ART

Compounds with intense light absorption in 550 to 620 nm, particularly compounds having a wavelength of absorption maximum ($\lambda$max) in 550 to 620 nm, are used as optical recording materials for forming optical recording layers of optical recording media such as DVD-R.

As the above optical recording materials, there are many reports with cyanine compounds having an indole ring since they have merits of high sensitivity and compatibility with high-speed recording. For example, Patent Documents 1 and 2 report low temperature-decomposable cyanine compounds in which a metallocene-containing group is introduced into a side chain on the nitrogen atom, whereas Patent Document 3 reports low temperature-decomposable cyanine compounds in which a benzyl group is introduced into the position-3. Patent Document 1 also describes use of perchlorate as an anion component of cyanine compounds can further decrease the decomposition temperature.

If the optical recording material used in the optical recording layer of optical recording medium releases large heat on its decomposition, recording properties will be deteriorated due to thermal interference of recording pits. Optical recording materials are, therefore, desired to decompose not only at lower temperature but also less exothermically. For example, cyanine compounds containing perchlorate anion, which is effective for lowering the decomposition temperature, release large heat on decomposition, possibly deteriorating jitter properties of optical recording media.

Patent Document 1: Japanese Patent Laid-open Publication No. 2003-171571
Patent Document 2: Japanese Patent Laid-open Publication No. 2004-195765
Patent Document 3: Japanese Patent Laid-open Publication No. 2003-231359

DISCLOSURE OF THE INVENTION

Problems to be Solved by the Invention

An object of the present invention is, therefore, to provide a cyanine compound exhibiting decomposition behavior suitable for an optical recording material used in an optical recording layer of an optical recording medium for high-speed recording, and an optical recording material comprising the compound.

Means for Solving the Problems

After extensive study, the present inventors have found that cyanine compounds with a particular cationic structure have good thermal properties as optical recording materials.

The present invention is based on the above findings and provides a cyanine compound represented by general formula (I) below and an optical recording material comprising the cyanine compound used in an optical recording layer of an optical recording medium in which the optical recording layer is formed on a substrate.

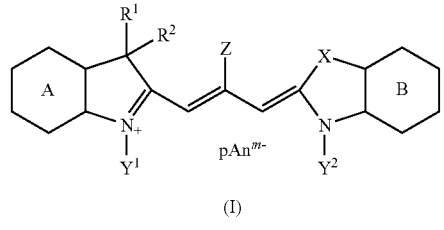

[Formula 1]

(I)

(In the formula, ring A and ring B each represent an optionally substituted benzene or naphthalene ring; X represents O, S, Se, $CR^3R^4$, or NY; at least one of $R^1$ and $R^2$ represents a group represented by general formula (II) or (III) below, and when only one of them is a group represented by general formula (II) or (III), the other represents an organic group having 1 to 30 carbon atoms; $R^3$ and $R^4$ each represent an organic group having 1 to 30 carbon atoms; Y represents a hydrogen atom or an organic group having 1 to 30 carbon atoms; at least one of $Y^1$ and $Y^2$ is a group represented by general formula (IV) below, and when only one of $Y^1$ and $Y^2$ is a group represented by general formula (IV), the other represents a hydrogen atom or an organic group having 1 to 30 carbon atoms; Z represents a hydrogen atom, a halogen atom, or a cyano group; $An^{m-}$ represents an m-valent anion; m is an integer of 1 or 2; and p represents a coefficient to keep the electric charge neutral.)

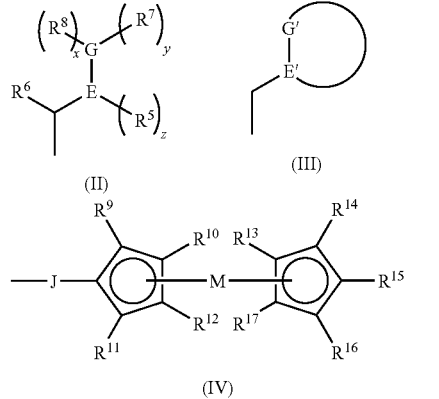

[Formula 2]

(II)  (III)

(IV)

(In general formula (II), the bond between E and G is a double or triple bond; E represents a carbon atom; G represents a carbon, oxygen, or nitrogen atom; each of x, y, and z represents 0 or 1; $R^5$ represents a hydrogen atom, a halogen atom, an optionally halogenated alkyl group having 1 to 4 carbon atoms, or an optionally halogenated alkoxy group having 1 to 4 carbon atoms; each of $R^6$, $R^7$, and $R^8$ independently represents a hydrogen atom, a halogen atom, or an optionally halogenated alkyl group having 1 to 4 carbon atoms; and $R^6$ and $R^8$ may bond to form a ring system. In general formula (III), the bond between E' and G' is a double bond; E' represents a carbon atom; G' represents a carbon, oxygen, or nitrogen atom; the ring containing E' and G' represents a five-membered ring optionally containing (a) heteroatom(s), a six-membered ring containing (a) heteroatom(s), a benzene ring, a naphthalene ring, a quinoline ring, an isoquinoline ring, an anthracene ring, or an anthraquinone ring; and these rings containing E' and G' may be substituted with a hydroxyl group, a halogen atom, a nitro group, a cyano group, an alkyl group, or an alkoxy group. In general formula (IV), $R^9$ to $R^{17}$ each represent a hydrogen atom, or an optionally halogenated alkyl group having 1 to 4 carbon atoms in which (a) methylene group(s) in the chain may be replaced by —O— or —CO—; M represents Fe, Co, Ni, Ti, Cu, Zn, Zr, Cr, Mo, Os, Mn, Ru, Sn, Pd, Rh, or Pt; and J represents a direct bond or an alkylene group having 1 to 8 carbon atoms in which (a) methylene group(s) in the alkylene group may be replaced by —O—, —S—, —CO—, —COO—, —OCO—, —SO$_2$—, —NH—, —CONH—, —NHCO—, —N=CH—, or —CH=CH—.)

BRIEF DESCRIPTION OF DRAWINGS

[FIG. 1]
FIG. 1 is the $^1$H-NMR spectrum of a cyanine compound (hexafluoro-phosphate of compound No. 4) of the present invention obtained in Example 1.

BEST MODE FOR CARRYING OUT THE INVENTION

The cyanine compound of the present invention represented by general formula (I) is a compound comprising a group with particular structure on the position-3 of the indole ring and another particular group in the side chain on the nitrogen atom. The cyanine compound has a decomposition temperature lower than those of conventional cyanine compounds used as optical recording materials for application of DVD-R, and is compatible with high-speed recording.

In general formula (I), the substituent in the optionally substituted benzene or naphthalene ring represented by ring A or ring B includes a halogen atom such as fluorine, chlorine, bromine, and iodine; an optionally halogenated alkyl group such as methyl, ethyl, propyl, isopropyl, butyl, sec-butyl, tert-butyl, isobutyl, amyl, isoamyl, tert-amyl, hexyl, cyclohexyl, heptyl, isoheptyl, tert-heptyl, n-octyl, isooctyl, tert-octyl, 2-ethylhexyl, and trifluoromethyl; an aryl group such as phenyl, naphthyl, 2-methylphenyl, 3-methylphenyl, 4-methylphenyl, 4-vinylphenyl, and 3-isopropylphenyl; an optionally halogenated alkoxy group such as methoxy, ethoxy, propoxy, isopropoxy, butoxy, sec-butoxy, tert-butoxy, and trifluoromethyloxy; an alkylthio group such as methylthio, ethylthio, propylthio, isopropylthio, butylthio, sec-butylthio, tert-butylthio, and trifuoromethylthio; a nitro group, a cyano group, and the like.

In general formula (I), the organic group having 1 to 30 carbon atoms represented by $R^1$ to $R^4$, Y, $Y^1$, or $Y^2$ includes, but is not limited thereto, for example, an alkyl group such as methyl, ethyl, propyl, isopropyl, butyl, sec-butyl, tert-butyl, isobutyl, amyl, isoamyl, tert-amyl, hexyl, cyclohexyl, cyclohexylmethyl, 2-cyclohexylethyl, heptyl, isoheptyl, tert-heptyl, n-octyl, isooctyl, tert-octyl, 2-ethylhexyl, nonyl, isononyl, decyl, dodecyl, tridecyl, tetradecyl, pentadecyl, hexadecyl, heptadecyl, and octadecyl; an alkenyl group such as vinyl, 1-methylethenyl, 2-methylethenyl, propenyl, butenyl, isobutenyl, pentenyl, hexenyl, heptenyl, octenyl, decenyl, pentadecenyl, and 1-phenylpropen-3-yl; an alkylaryl group such as phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl)phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, and cyclohexylphenyl; an aralkyl group such as benzyl, phenethyl, 2-phenylpropan-2-yl, diphenylmethyl, triphenylmethyl, styryl, and cinnamyl; and a group having a structure wherein the hydrocarbon group just listed is interrupted by (an) ether bond(s) and/or (a) thioether bond(s), for example, 2-methoxyethyl, 3-methoxypropyl, 4-methoxybutyl, 2-butoxyethyl, methoxyethoxyethyl, methoxyethoxyethoxyethyl, 3-methoxybutyl, 2-phenoxyethyl, 2-methylthioethyl, and 2-phenylthioethyl. These groups may be further substituted with an alkoxy group, an alkenyl group, a nitro group, a cyano group, a halogen atom, or the like.

When any substituent represented by $R^1$ to $R^4$ in general formula (I) is bulky, the molar absorption coefficient of cyanine compound becomes small, possibly affecting sensitivity, or steric hindrance might substantially reduce productivity in manufacturing the cyanine compound. Therefore, $R^1$ to $R^4$ are preferably groups listed below. At least either of $R^1$ or $R^2$ is preferably the optionally substituted benzyl group below, which is a group represented by general formula (III).

Preferred groups for $R^1$ to $R^4$ include:
alkyl groups such as methyl, ethyl, propyl, isopropyl, butyl, sec-butyl, tert-butyl, and isobutyl, particularly an alkyl group having 1 to 4 carbon atoms; and
optionally substituted benzyl groups, wherein the substituent includes a hydroxyl group; a halogen atom such as fluorine, chlorine, bromine, and iodine; a cyano group; a nitro group; an alkyl group having 1 to 4 carbon atoms such as methyl, ethyl, propyl, isopropyl, butyl, sec-butyl, tert-butyl, and isobutyl; a haloalkyl group having 1 to 4 carbon atoms such as chloromethyl, dichloromethyl, trichloromethyl, bromomethyl, dibromomethyl, tribromomethyl, fluoromethyl, difluoromethyl, trifluoromethyl, 2,2,2-trifluoroethyl, perfluoroethyl, perfluoropropyl, and perfluorobutyl; an alkoxy group having 1 to 4 carbon atoms such as methoxy, ethoxy, propoxy, isopropoxy, butoxy, sec-butoxy, and tert-butoxy; a haloalkoxy group having 1 to 4 carbon atoms such as chloromethyloxy, dichloromethyloxy, trichloromethyloxy, bromomethyloxy, dibromomethyloxy, tribromomethyloxy, fluoromethyloxy, difluoromethyloxy, trifluoromethyloxy, 2,2,2-trifluoroethyloxy, perfluoroethyloxy, perfluoropropyloxy, and perfluorobutyloxy; and the like.

$R^3$ and $R^4$ may be linked to form a three- to six-membered cyclic group. The group forming a three- to six-membered ring includes cyclopropane-1,1,-diyl, cyclobutane-1,1-diyl, 2,4-dimethylcyclobutane-1,1-diyl, 3,3-dimethylcyclobutane-1,1-diyl, cyclopentane-1,1-diyl, cyclohexane-1,1-diyl, tetrahydropyran-4,4-diyl, thiane-4,4-diyl, piperidine-4,4-diyl, N-substituted piperidine-4,4-diyl, morpholine-2,2-diyl, morpholine-3,3-diyl, N-substituted morpholine-2,2-diyl, N-substituted morpholine-3,3-diyl, and the like, wherein the substituent on the nitrogen atom includes those listed as the substituents on ring A and ring B.

In general formula (I), each of $Y^1$ and $Y^2$ is, if not the group represented by general formula (IV), a hydrogen atom or an organic group having 1 to 30 carbon atoms. If a bulky substitutent is introduced as the organic group, the molar absorption coefficient of the cyanine compound becomes small, possibly affecting sensitivity, so that the organic group having 1 to 30 carbon atoms represented by $Y^1$ and $Y^2$ is preferably a hydrocarbon group having 1 to 8 carbon atoms, and more preferably an alkyl group having 1 to 8 carbon atoms. When X is NY, the organic group having 1 to 30 carbon atoms represented by Y is, from similar viewpoint, preferably a hydrocarbon group having 1 to 8 carbon atoms, and more preferably an alkyl group having 1 to 8 carbon atoms.

In general formula (I), the halogen atom represented by Z includes fluorine, chlorine, bromine, and iodine atoms.

Among the cyanine compounds of the present invention, the compound having $CR^3R^4$ as X in general formula (I) is preferred, since its absorption wavelength is suitable for use as an optical recording material used for optical recording layers in optical recording media with which semiconductor lasers emitting at 550 to 620 nm are used.

In general formula (I), the anion represented by $An^{m-}$ includes, for example, as a monovalent anion, halogen anions such as chloride, bromide, iodide, and fluoride; inorganic anions such as perchlorate, chlorate, thiocyanate, hexafluorophosphate, hexafluoroantimonate, and tetrafluoroborate; organic sulfonate anions such as benzenesulfonate, toluenesulfonate, trifluoromethanesulfonate, diphenylamine-4-sulfonate, 2-amino-4-methyl-5-chlorobenzenesulfonate, and 2-amino-5-nitrobenzenesulfonate; organic phosphate anions such as octylphosphate, dodecylphosphate, octadecylphosphate, phenylphosphate, nonylphenylphosphate, 2,2'-methylenebis(4,6-di-tert-butylphenyl)phosphonate; and the like, and as a divalent anions, benzenedisulfonate, naphthalenedisulfonate, and the like. There may be also used, if necessary, a metal complex-type quencher anion, which has a function to deactivate (quench) an active molecule in an excited state, or an anion derived from a metallocene compound such as ferrocene and ruthenocene having an anionic group such as a carboxyl, phospho, or sulfo group on its cyclopentadienyl ring(s).

The metal complex-type quencher anion includes, for example, azo chelate complexes, anions represented by general formula (A) or (B) below, the anions described in Japanese Patent Laid-open Publication No. S60-234892, Japanese Patent Laid-open Publication No. H5-43814, Japanese Patent Laid-open Publication No. H6-239028, Japanese Patent Laid-open Publication No. H9-309886, Japanese Patent Laid-open Publication No. H10-45767, and the like.

[Formula 9]

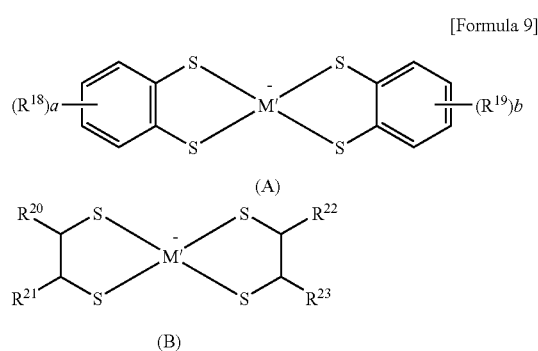

(In the formulae, M' represents a nickel or copper atom; $R^{18}$ and $R^{19}$ each represent a halogen atom, an alkyl group having 1 to 8 carbon atoms, an aryl group having 6 to 30 carbon atoms, or $-SO_2-Z'$; Z' represents an alkyl, optionally halogenated aryl, dialkylamino, diarylamino, piperidino, or morpholino group; and a and b each represent a number of 0 to 4. Each of $R^{20}$, $R^{21}$, $R^{22}$, and $R^{23}$ independently represents an alkyl, alkylphenyl, alkoxyphenyl, or halogenated phenyl group.)

The cyanine compounds having perchlorate as the anion represented by $An^{m-}$ in general formula (I) release large heat on decomposition and has a characteristically low decomposition temperature, potentially worsening jitter due to thermal interference of pits. Therefore, when the cyanine compounds of the present invention are used as optical recording materials, the anion is preferably other than perchlorate.

In general formula (II), the halogen atom represented by $R^5$ to $R^8$ includes fluorine, chlorine, bromine, and iodine. The optionally halogenated alkyl group having 1 to 4 carbon atoms represented by $R^5$ to $R^8$ includes methyl, ethyl, propyl, isopropyl, butyl, sec-butyl, tert-butyl, isobutyl, chloromethyl, dichloromethyl, trichloromethyl, bromomethyl, dibromomethyl, tribromomethyl, fluoromethyl, difluoromethyl, trifluoromethyl, 2,2,2-trifluoroethyl, perfluoroethyl, perfluoropropyl, perfluorobutyl, and the like. The optionally halogenated alkoxy group having 1 to 4 carbon atoms represented by $R^5$ includes methoxy, ethoxy, propoxy, isopropoxy, butoxy, sec-butoxy, tert-butoxy, trifluoromethyloxy, and the like. The ring system formed by bonding of $R^6$ and $R^8$ includes cyclobutene, cyclopentene, cyclohexene, pyrrole, dihydropyrrole, and pyridine ring, and the like.

In general formula (III), the five-membered ring containing E', G', and optionally (a) heteroatom(s) includes cyclopentene, cyclopentadiene, pyrrole, imidazole, pyrazole, triazole, thiophene, furan, thiazole, isothiazole, oxazole, isooxazole, dihydropyrrole, dihydroimidazole, dihydropyrazole, dihydrothiophene, dihydrofuran, dihydrothiazole, dihydroisothiazole, dihydrooxazole, and dihydroisooxazole rings and the like. The six-membered ring containing E', G', and (a) heteroatom(s) includes pyridine, pyrazine, pyrimidine, pyridazine, pyran, and thiopyran rings and the like. These rings containing E' and G' may be substituted with a halogen atom such as fluorine, chlorine, bromine, and iodine; a nitro group; a cyano group; an alkyl group such as methyl, ethyl, propyl, isopropyl, butyl, isobutyl, tert-butyl, and trifluoromethyl; or an alkoxy group such as methoxy, ethoxy, propoxy, isopropoxy, butoxy, sec-butoxy, tert-butoxy, and trifluoromethyloxy.

In general formula (IV), the alkyl group having 1 to 4 carbon atoms represented by $R^9$ to $R^{17}$ includes methyl, ethyl, propyl, isopropyl, butyl, sec-butyl, tert-butyl, and isobutyl. The halogenated derivatives of these alkyl groups include chloromethyl, dichloromethyl, trichloromethyl, bromomethyl, dibromomethyl, tribromomethyl, fluoromethyl, difluoromethyl, trifluoromethyl, 2,2,2-trifluoroethyl, perfluoroethyl, perfluoropropyl, perfluorobutyl, and the like. The group wherein (a) methylene group(s) in the chain of such alkyl group is replaced by —O— includes methoxy, ethoxy, propoxy, isopropoxy, butoxy, sec-butoxy, tert-butoxy, 2-methoxyethoxy, 2-methoxyethyl, chloromethyloxy, dichloromethyloxy, trichloromethyloxy, bromomethyloxy, dibromomethyloxy, tribromomethyloxy, fluoromethyloxy, difluoromethyloxy, trifluoromethyloxy, 2,2,2-trifluoroethyloxy, perfluoroethyloxy, perfluoropropyloxy, perfluorobutyloxy, and the like. The group wherein (a) methylene group(s) in the chain of such alkyl group is replaced by —CO— includes acetyl, propionyl, monochloroacetyl, dichloroacetyl, trichloroacetyl, trifluoroacetyl, propan-2-on-1-yl, butan-2-on-1-yl, and the like.

In general formula (IV), the alkylene group having 1 to 8 carbon atoms represented by J includes methylene, ethylene, propylene, methylethylene, butylene, 1-methylpropylene, 2-methylpropylene, 1,2-dimethylpropylene, 1,3-dimethylpropylene, 1-methylbutylene, 2-methylbutylene, 3-methylbutylene, 4-methylbutylene, 2,4-dimethylbutylene, 1,3-dimethylbutylene, pentylene, hexylene, heptylene, octylene, ethane-1,1-diyl, propane-2,2-diyl, cyclopropane-1,1-diyl, cylcopropane-1,2-diyl, cyclobutane-1,1-diyl, cyclobutane-1,2-diyl, cyclopentane-1,1-diyl, cyclopentane-1,2-diyl, cyclopentane-1,3-diyl, cyclohexane-1,1-diyl, cyclohexane-1,2-diyl, cyclohexane-1,3-diyl, cyclohexane-1,4-diyl, methylcyclohexane-1,4-diyl, and the like. In the group in which (a) methylene group(s) in the alkylene group is(are) replaced by —O—, —S—, —CO—, —COO—, —OCO—, —SO$_2$—, —NH—, —CONH—, —NHCO—, —N=CH—, or —CH=CH—, the number and position of replacement may be arbitrarily selected.

The cyanine compound of the present invention having a group represented by general formula (IV) wherein M is Fe and J is an alkylene group having 1 to 8 carbon atoms are preferred because of low production cost and excellent light fastness.

Specific examples of the cyanine compounds of the present invention represented by general formula (I) include compounds No. 1 to No. 45 below. Examples illustrated below are given as a cyanine cation with any anion omitted.

[Formula 4]

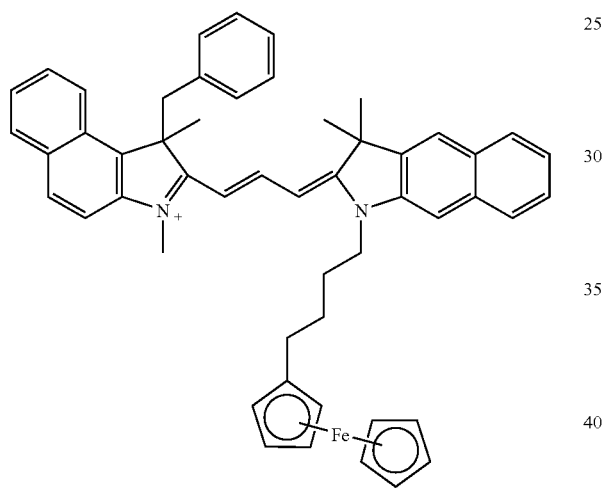

Compound No. 1

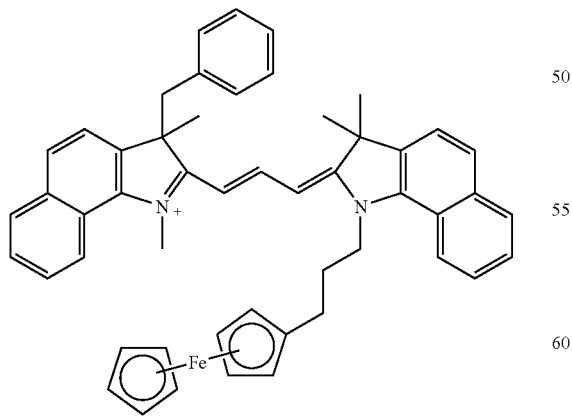

Compound No. 2

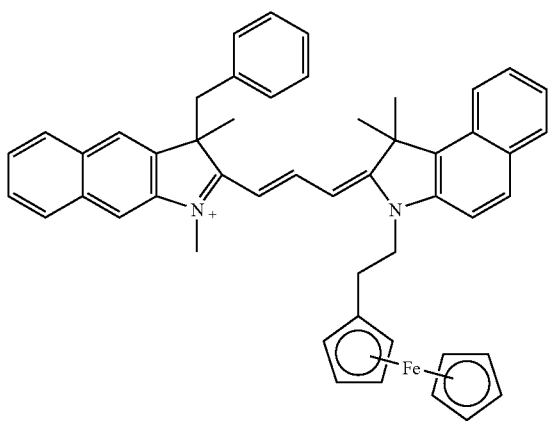

Compound No. 3

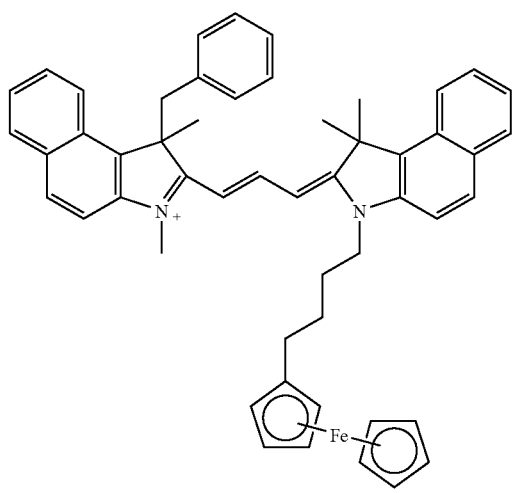

Compound No. 4

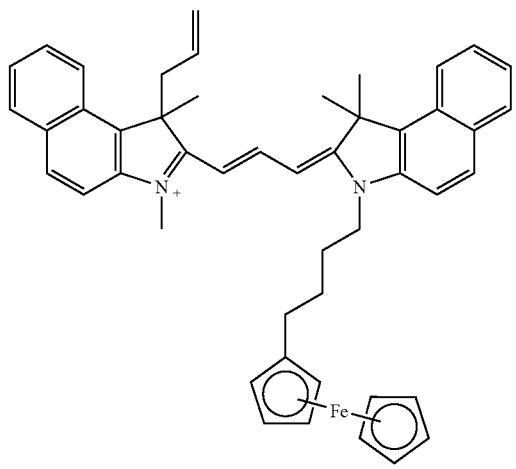

Compound No. 5

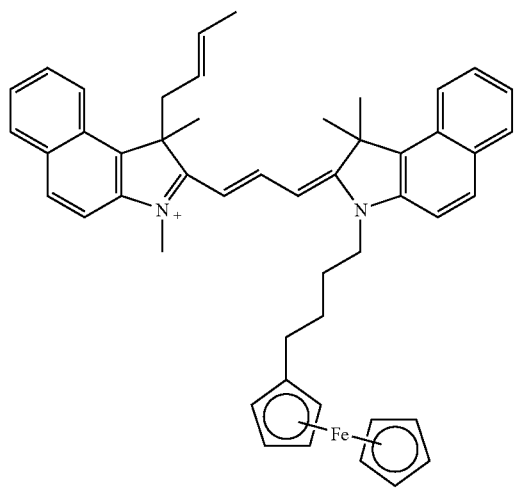
Compound No. 6
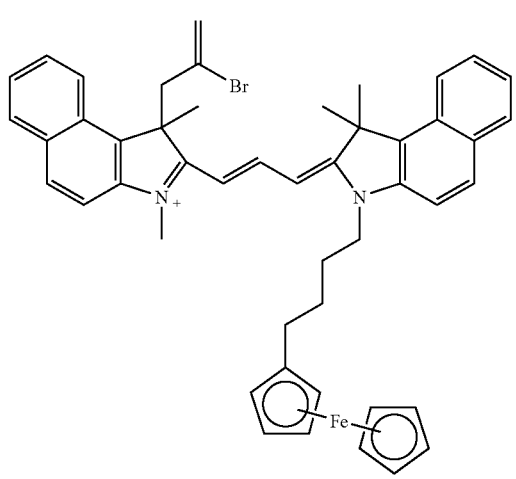
Compound No. 9
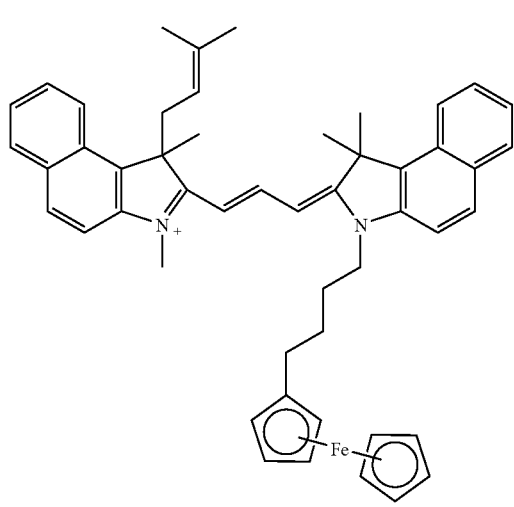
Compound No. 7
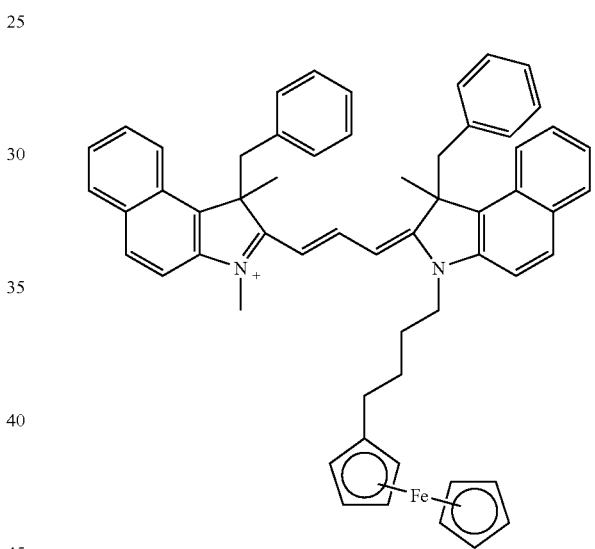
Compound No. 10
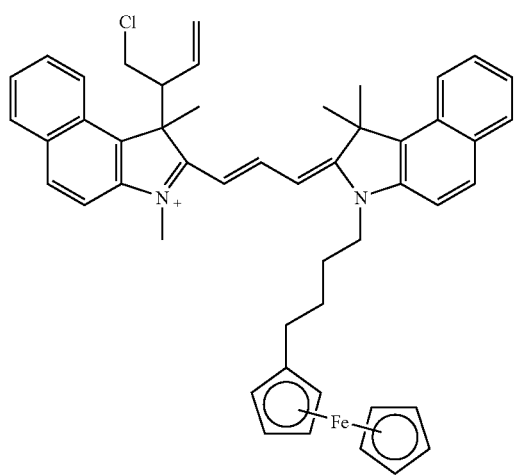
Compound No. 8
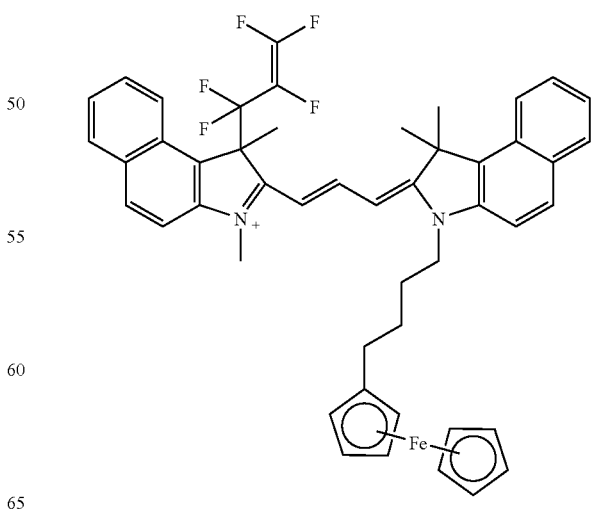
Compound No. 11

-continued
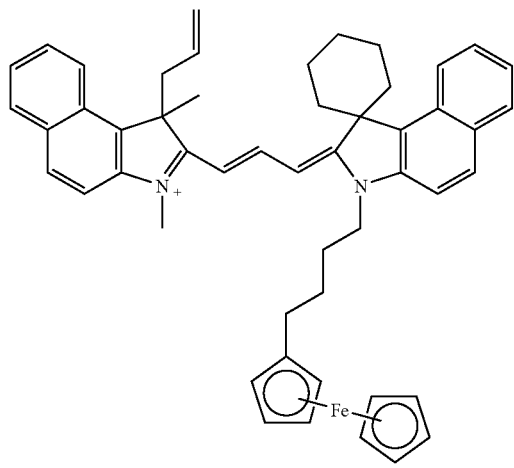
Compound No. 12
[Formula 5]
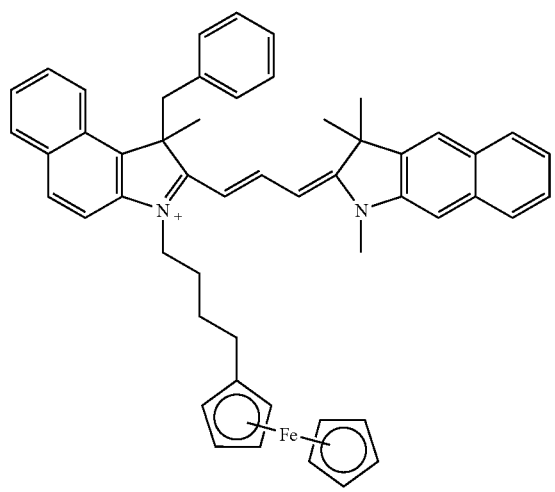
Compound No. 13
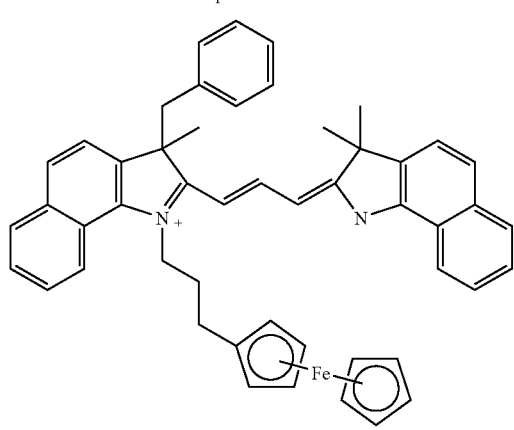
Compound No. 14
-continued
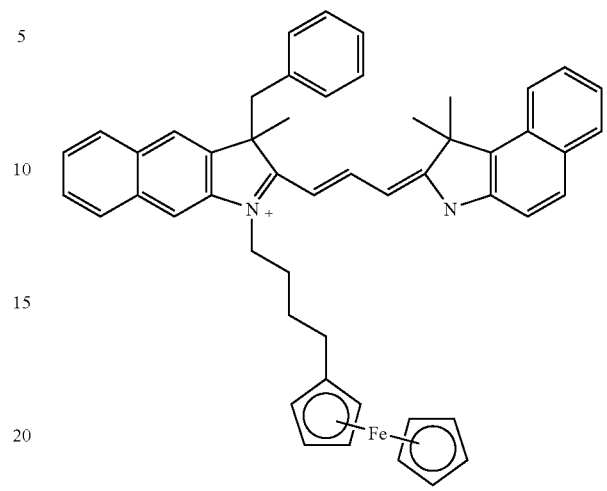
Compound No. 15
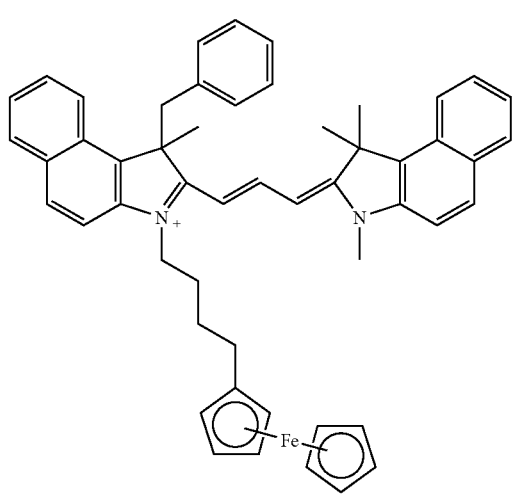
Compound No. 16
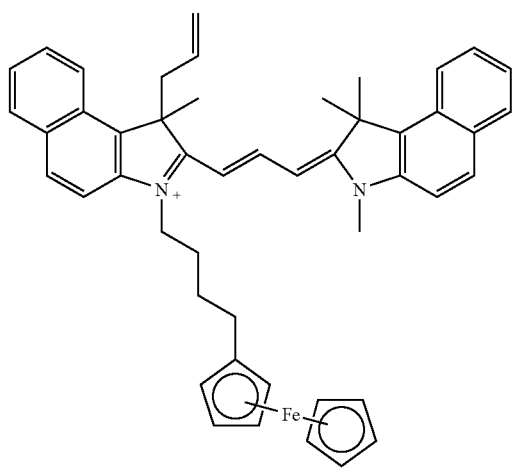
Compound No. 17

-continued
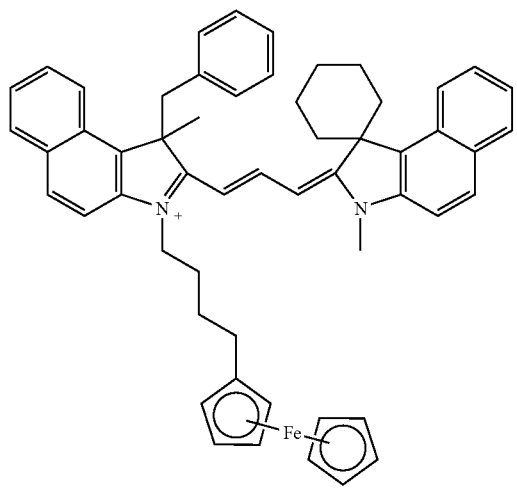
Compound No. 18
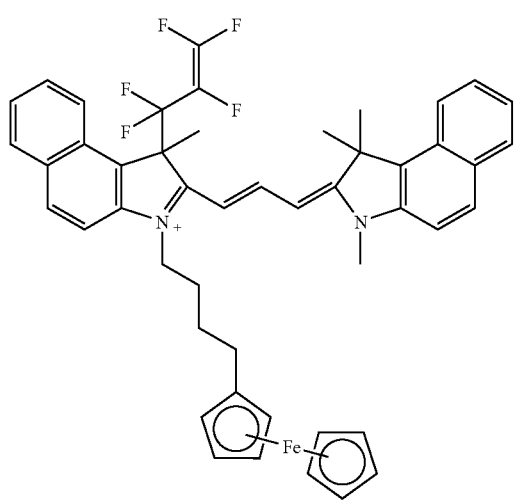
Compound No. 19
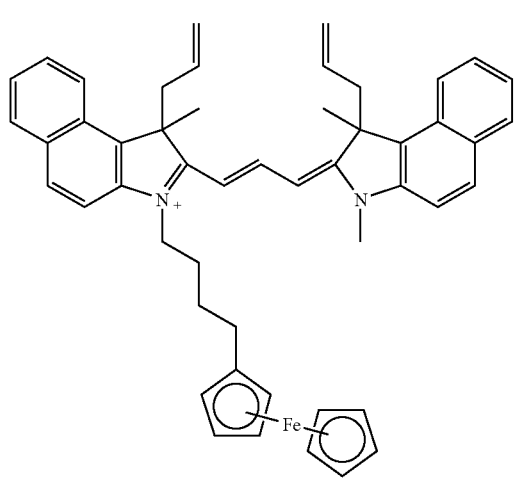
Compound No. 20
-continued
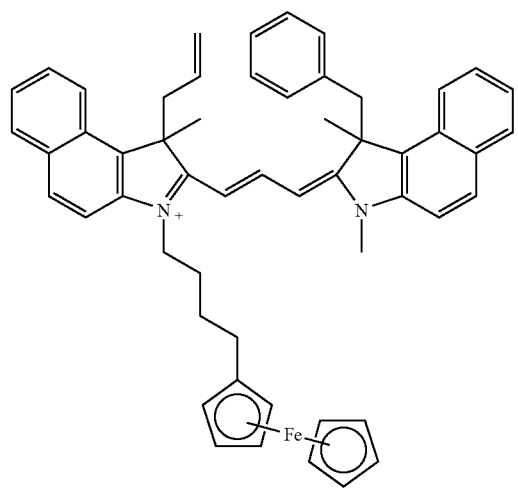
Compound No. 21
[Formula 6]
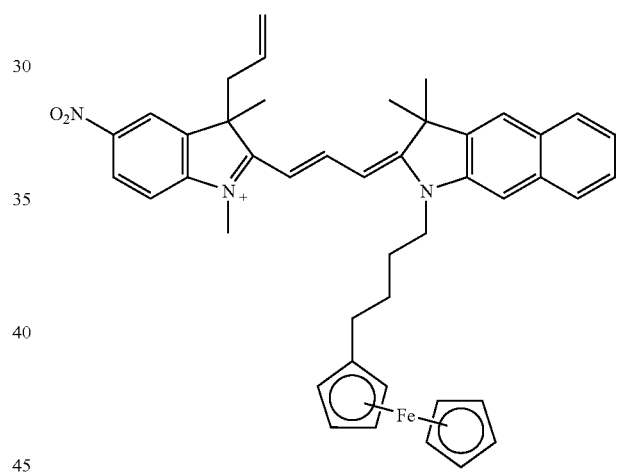
Compound No. 22
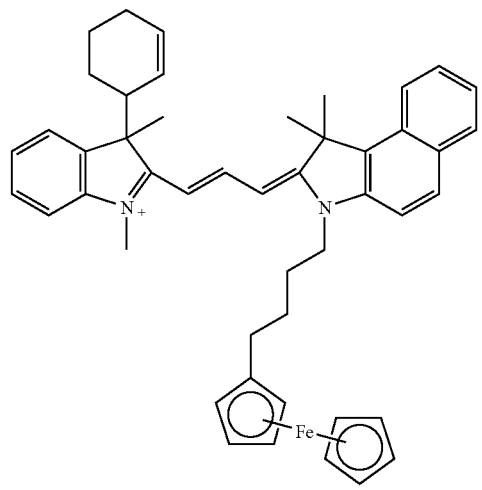
Compound No. 23

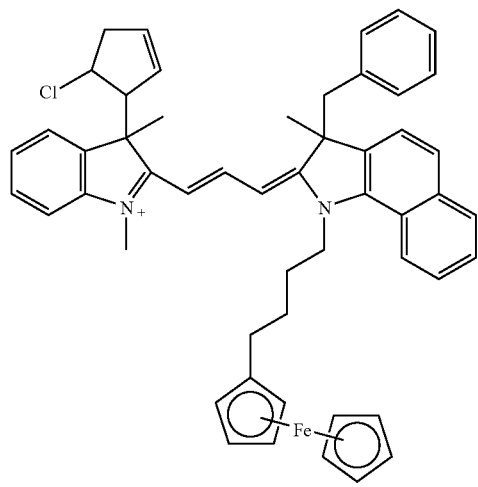
Compound No. 24
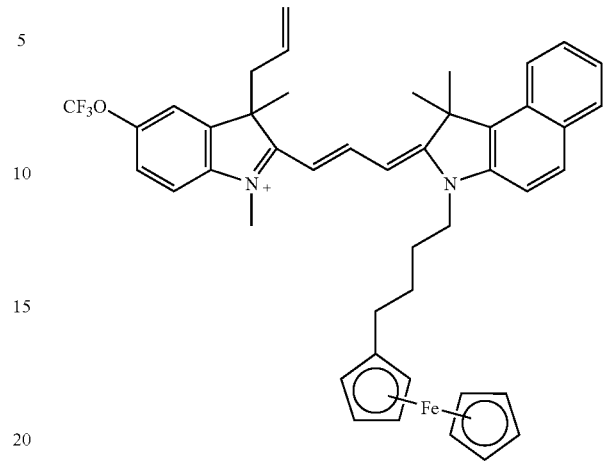
Compound No. 27
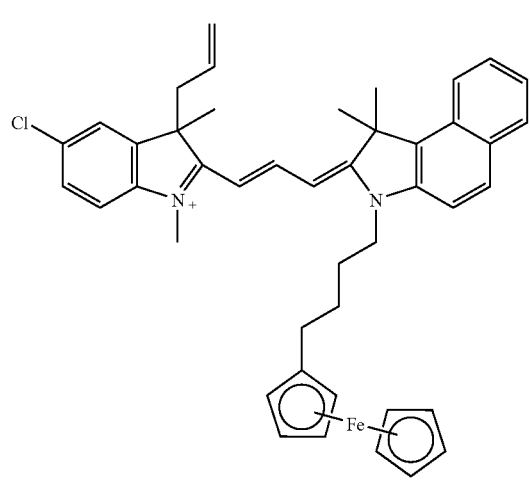
Compound No. 25
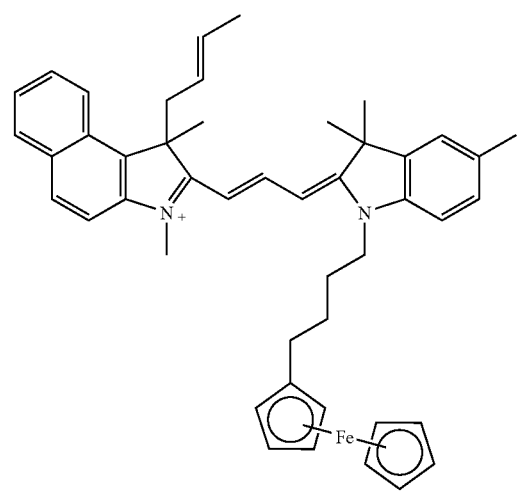
Compound No. 28
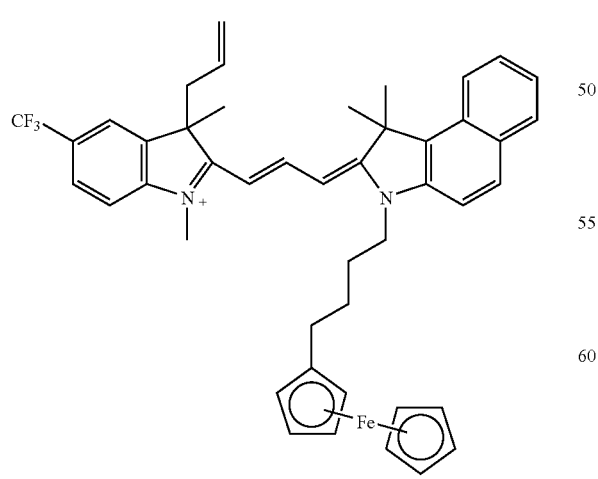
Compound No. 26
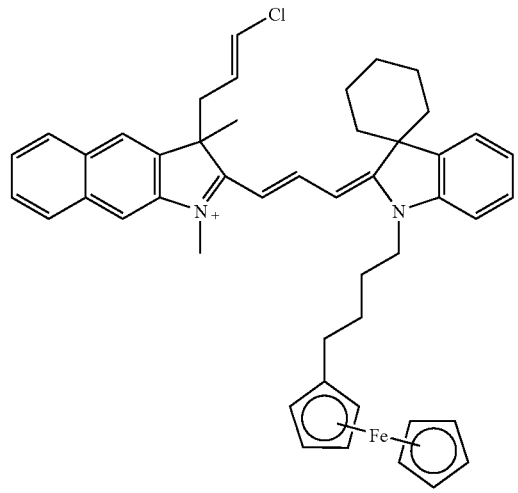
Compound No. 29

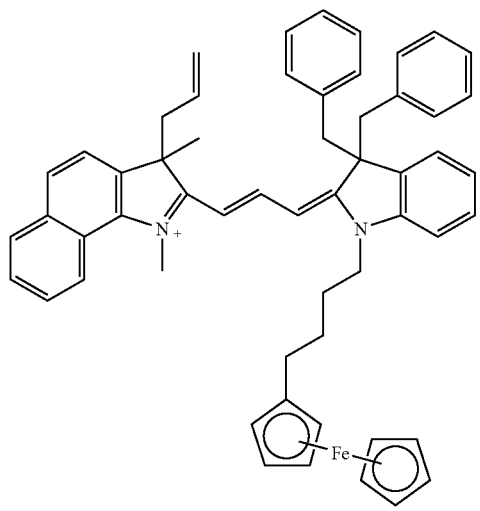
Compound No. 30
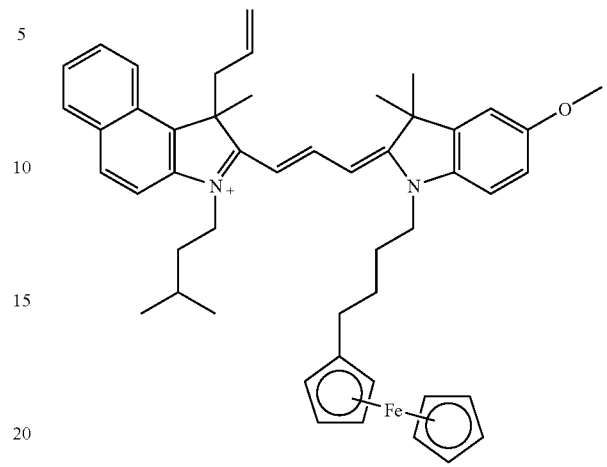
Compound No. 33
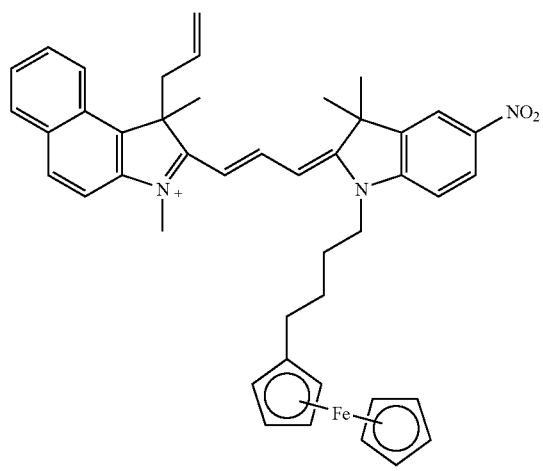
Compound No. 31
[Formula 7]
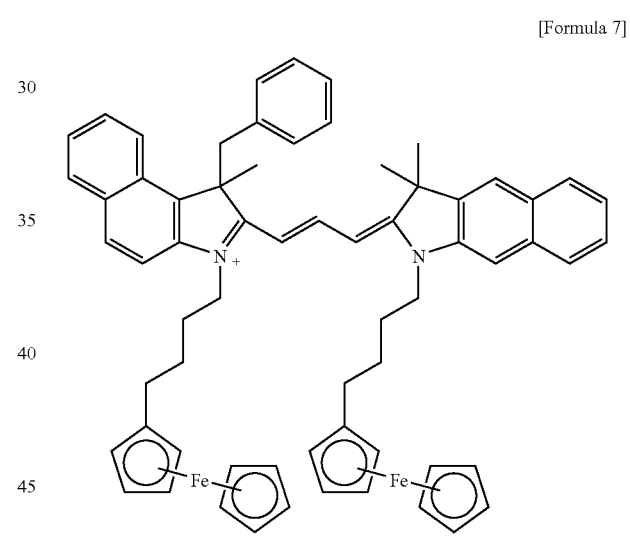
Compound No. 34
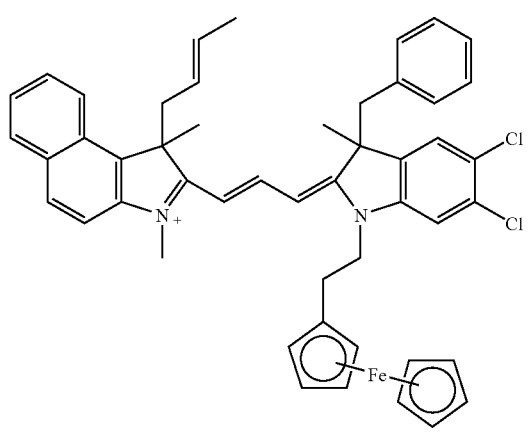
Compound No. 32
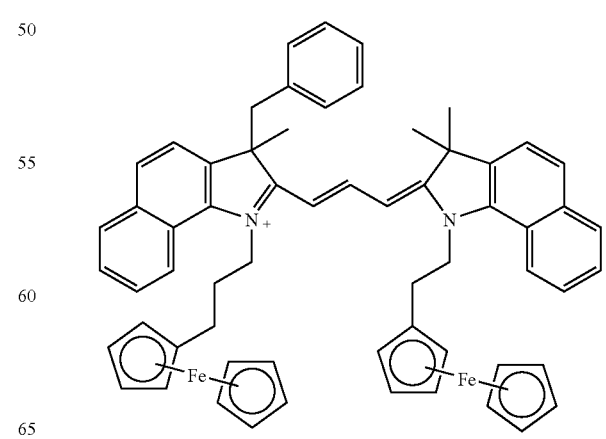
Compound No. 35

-continued
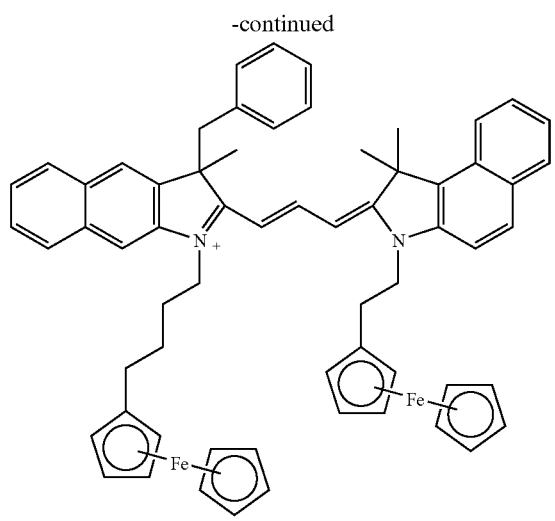
Compound No. 36
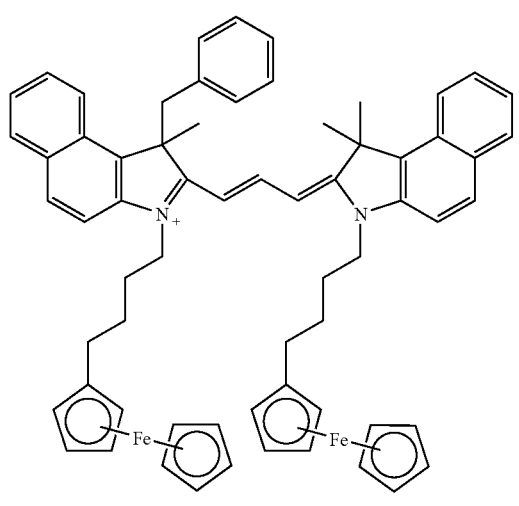
Compound No. 37
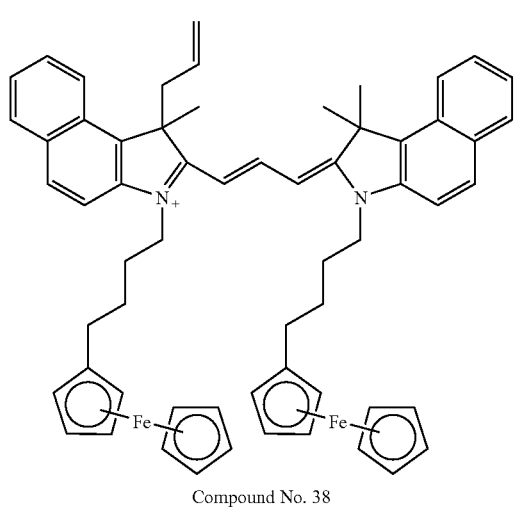
Compound No. 38
-continued
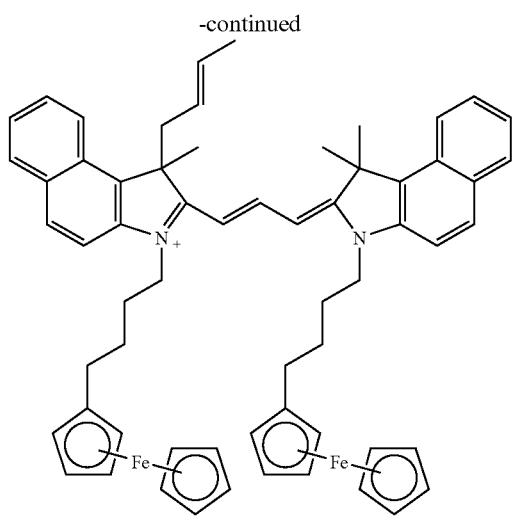
Compound No. 39
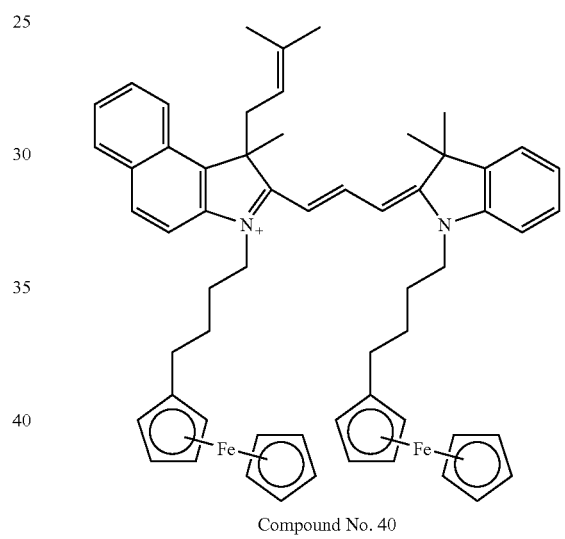
Compound No. 40
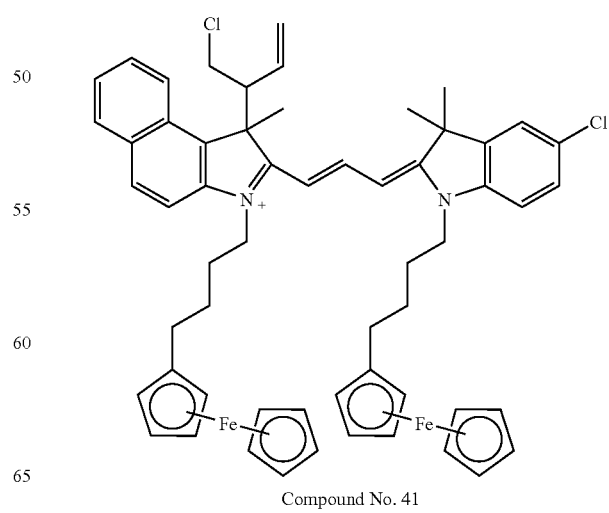
Compound No. 41

-continued

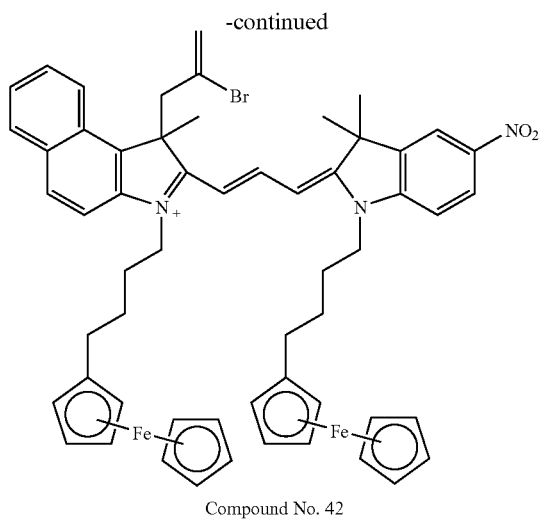

Compound No. 42

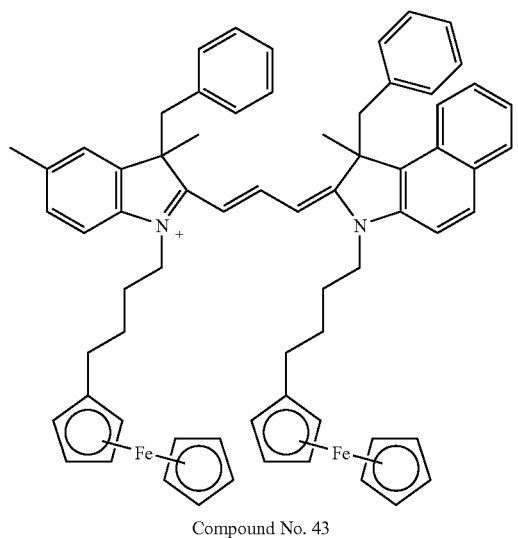

Compound No. 43

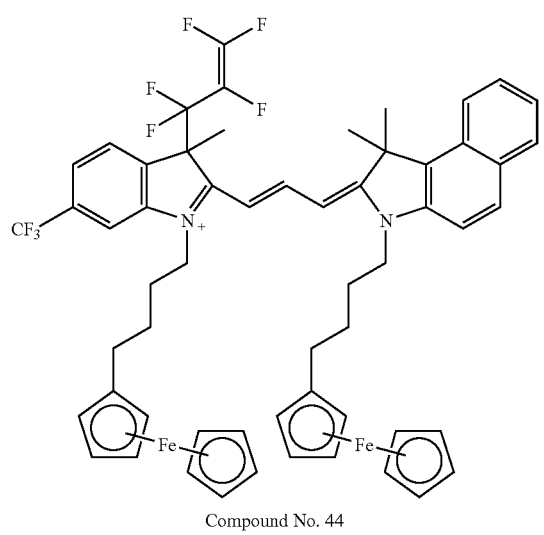

Compound No. 44

-continued

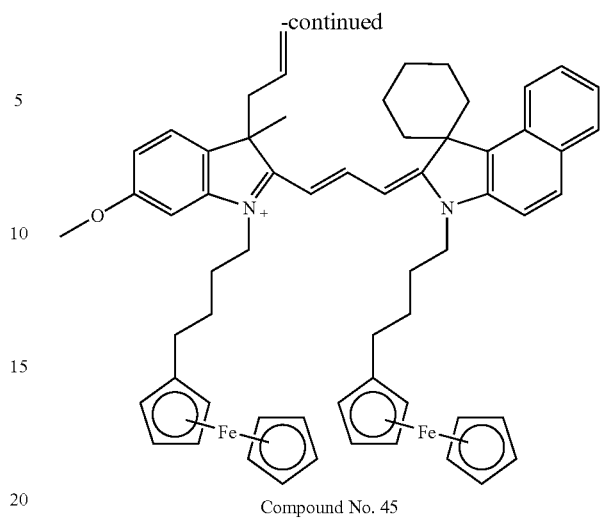

Compound No. 45

The cyanine compound of the present invention represented by general formula (I) are not limited by the manufacturing method. Such cyanine compound can be obtained, for example, by reaction of a quaternary salt of 2-methylindole derivative, an intermediate, with a bridging agent such as N,N'-diphenylformamidine. The multiple bond-containing group represented by general formula (II) or (III) can be introduced in a process to obtain a quaternary salt of 2-methylindole derivative as an intermediate. Such methods include, for example, a method in which an arylhydrazine derivative as a starting material is reacted with a 2-butanone derivative having the multiple bond-containing group represented by general formula (II) or (III) to form an indole ring accompanied by introduction of the group, a method in which an indole ring is reacted with a halogenated derivative having the group to be introduced, and the like. Y, $Y^1$, and $Y^2$ can be introduced from Y-D, $Y^1$-D, and $Y^2$-D (D being a halogen atom such as chlorine, bromine, and iodine or a sulfonyloxy group such as phenylsulfonyloxy, 4-methylphenylsulfonyloxy, and 4-chlorophenylsulfonyloxy), respectively, which are reactive to an arylamine derivative or NH group of indole ring. The 2-butanone derivative having the multiple bond-containing group represented by general formula (II) or (III) can be obtained by reaction of acetone with benzaldehyde having the corresponding substituent.

The method for introducing the group represented by general formula (IV) includes, for example, the method described in Patent Document 1.

The optical recording material of the present invention is used to form an optical recording layer of an optical recording medium in which the optical recording layer is formed as a thin film on a substrate. The optical recording material includes the cyanine compounds of the present invention themselves represented by general formula (I) and any mixtures of the cyanine compound(s) and organic solvent(s) and/or various compound(s) described below.

The method for forming the optical recording layer of the optical recording medium using the optical recording material of the present invention is not particularly limited. Generally a wet coating method is used, in which the cyanine compound of the present invention and, optionally, various compounds described below are dissolved in an organic solvent to form a solution and this solution is applied to a substrate by spin-coating, spraying, dip-coating, or the like. The organic solvent used here includes lower alcohols such as methanol and ethanol; ether alcohols such as methyl cellosolve, ethyl cellosolve, butyl cellosolve, and butyl diglycol; ketones such as acetone, methyl ethyl ketone, methyl isobutyl ketone, cyclohexanone, and diacetone alcohol; esters such as ethyl acetate, butyl acetate, and methoxyethyl acetate; acrylic esters such as ethyl acrylate and butyl acrylate; fluoroalcohols such as 2,2,2-trifluoroethanol, perfluoroethanol, 2,2,3,3-tetrafluoro-1-propanol, and perfluoropropanol; hydrocarbons such as benzene, toluene, and xylene; chlorohydrocarbons such as methylene dichloride, dichloroethane, and chloroform; and others. Methods other than wet coating include vapor deposition, sputtering, and the like.

Thickness of the above optical recording layer is, as a suitable range, generally 0.001 to 10μ, and preferably 0.01 to 5μ.

When the optical recording material of the present invention is contained in an optical recording layer of an optical recording medium, the content of the cyanine compound of the present invention represented by general formula (I) in the optical recording layer is preferably 25 to 100% by mass. In order to form the optical recording layer with such content of the cyanine compound, the optical recording material of the present invention preferably contains 25 to 100% by mass of the cyanine compound of the present invention with respect to the solid content in the optical recording material of the present invention.

The optical recording layer may contain, in addition to the cyanine compound of the present invention represented by general formula (I), as needed; dyestuffs used for optical recording layers such as other cyanine compounds, azo compounds, phthalocyanine compounds, oxonol compounds, squarilium compounds, styryl compounds, porphine compounds, and azo metal complexes; resins such as polyethylene, polyester, polystyrene, and polycarbonate; surfactants; antistatic agents; lubricants; fire retardants; radical scavengers such as hindered amines; pit formation promoters such as ferrocene derivatives; dispersants; antioxidants; crosslinking agents; light fastness improvers; or the like. The optical recording layer may also contain aromatic nitroso compounds, aminium compounds, iminium compounds, bisiminium compounds, transition metal chelate compounds, or others as a quencher of singlet oxygen or the like.

The amount of these compounds used in the optical recording layer is preferably in the range of 0 to 75% by mass. To that end, the content of these compounds is preferably 0 to 75% by mass in the optical recording material of the present invention based on the solid content of the optical recording material.

There are no particular limitations on the material of substrate on which the optical recording layer is formed so far as the material is substantially transparent to writing (recording) light and reading (playing-back) light. It includes, for example, resin such as polymethyl methacrylate, polyethylene terephthalate, and polycarbonate, glass, and the like. The shape of material may be in any form such as tape, drum, belt, and disc according to its application.

On the optical recording layer, a reflective film may be formed by vapor deposition or sputtering with gold, silver, aluminum, copper, or the like; and a protective layer may be also formed with acrylic resin, ultraviolet-curable resin, or the like.

The optical recording material of the present invention is suitable for optical recording media in which a semiconductor laser is used for recording and playing-back, particularly for optical discs such as DVD-R for high-speed recording.

The cyanine compound of the present invention can also be used, besides the optical recording materials, as a light-absorbing material for optical filters in image display devices such as liquid crystal displays and plasma displays.

EXAMPLE

The present invention will be described in more detail with Examples or others below. However, the present invention is not limited at all by Examples or others below.

Example 1

Production of Hexafluorophosphate of Compound No. 4

Hexafluorophosphate of compound No. 4 was obtained in 72% yield according to the synthetic route and synthetic procedure below.

(Synthetic route)

[Formula 8]

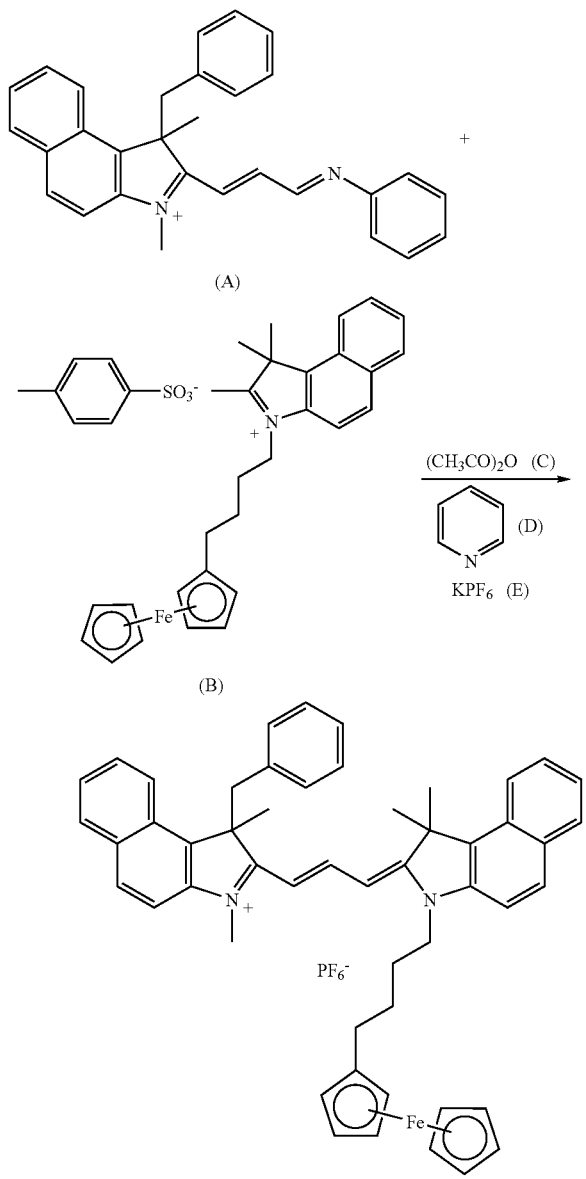

(Synthetic Procedure)

To a reaction flask were charged 0.003 mol of (A), 0.06 mol of (D), and 0.0042 mol of (C) shown in the above synthetic route, and the content was stirred. Here, 0.003 mol of (B) was added and the resultant mixture was stirred at 45° C. for 2.5 hours. Subsequently, here were added 0.0045 mol of (E) and 10 g of methanol and the mixture was stirred at 55° C. for 1 hour. After the mixture was allowed to stand stationary for 12 hours, crystals were collected by filtration, washed with methanol and water, and then dried under vacuum at 180° C. for 35 hours.

The dried crystals were analyzed to confirm this substance was the desired product, hexafluorophosphate of compound No. 4. The analytical results are shown below.

Optical properties (in chloroform, $3.60 \times 10^{-6}$ mol/l) λmax: 596 nm; ε: $1.26 \times 10^5$ Molecular weight (Time-of-flight mass spectrometric analysis) 904.8

Melting point (endothermic peak top in differential thermal analysis (DTA) at a heating speed of 10° C./min under nitrogen stream of 100 ml/min) 226.5° C.

$^1$H-NMR (solvent: DMSO)

The $^1$H-NMR spectrum is shown in FIG. 1.

Evaluation Example

Differential thermal analyses were carried out with hexafluorophosphate of compound No. 4 obtained in Example 1 and comparative compounds 1 to 3 shown below to determine the thermal decomposition temperature and heat released on decomposition. The thermal decomposition temperature was the temperature at exothermic peak top in DTA at a heating speed of 10° C./min under nitrogen atmosphere. The results are shown in Table 1.

[Formula 9]

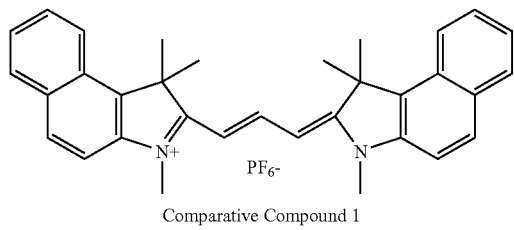

Comparative Compound 1

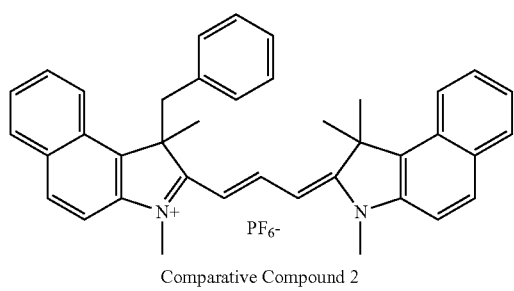

Comparative Compound 2

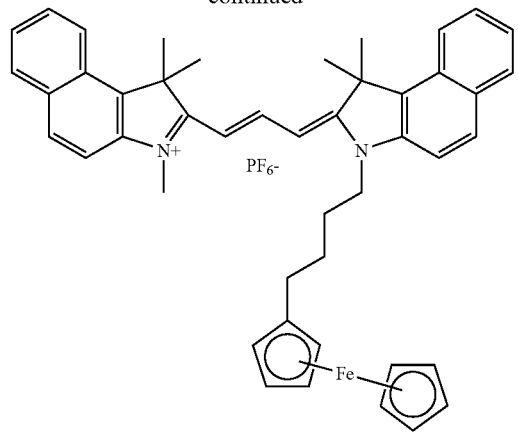

Comparative Compound 3

TABLE 1

| Cyanine compound | | Thermal decomposition |
|---|---|---|
| Cationic component | Anionic component | temperature (° C.) |
| Compound No. 4 | PF$^{6-}$ | 234 |
| Comparative compound 1 (Anionic component: PF$^{6-}$) | | 292 |
| Comparative compound 2 (Anionic component: PF$^{6-}$) | | 255 |
| Comparative compound 3 (Anionic component: PF$^{6-}$) | | 279 |

The results in Table 1 confirm the cyanine compound of the present invention is decomposed at a lower temperature as compared with similar cyanine compounds. This fact indicates the cyanine compound of the present invention exhibits thermal decomposition behavior suitable for use as an optical recording material.

INDUSTRIAL APPLICABILITY

The present invention provides a cyanine compound exhibiting suitable decomposition behavior for use as an optical recording material used in an optical recording layer of an optical recording medium for high-speed recording and an optical recording material comprising the compound.

The invention claimed is:

1. An optical recording medium comprising a recording layer on a substrate and at least one of a reflective layer and an ultraviolet cured protective layer, wherein the recording layer comprises a cyanine compound represented by general formula (I) below:

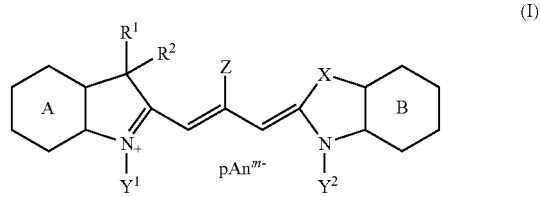

(I)

wherein, in the formula, ring A and ring B each represent an optionally substituted benzene or naphthalene ring; X represents O, S, Se, $CR^3R^4$, or NY; at least one of $R^1$ and $R^2$ represents a group represented by general formula (II) or (III) below and when only one of them is a group represented by general formula (II) or (III), the other represents an organic group having 1 to 30 carbon atoms; $R^3$ and $R^4$ each represents an organic group having 1 to 30 carbon atoms; Y represents a hydrogen atom or an organic group having 1 to 30 carbon atoms; at least one of $Y^1$ and $Y^2$ is a group represented by general formula (IV) below and when only one of $Y^1$ and $Y^2$ is a group represented by general formula (IV), the other represents a hydrogen atom or an organic group having 1 to 30 carbon atoms; Z represents a hydrogen atom, a halogen atom, or a cyano group; $An^{m-}$ represents an m-valent anion; m is an integer of 1 or 2; and p represents a coefficient to keep an electric charge neutral,

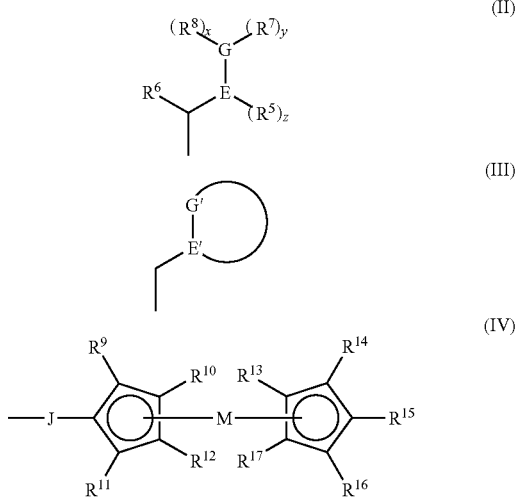

wherein in general formula (II), the bond between E and G is a double or triple bond; E represents a carbon atom; G represents a carbon, oxygen, or nitrogen atom; x, y, and z each represent 0 or 1; $R^5$ represents a hydrogen atom, a halogen atom, an optionally halogenated alkyl group having 1 to 4 carbon atoms, or an optionally halogenated alkoxy group having 1 to 4 carbon atoms; each of $R^6$, $R^7$, and $R^8$ independently represents a hydrogen atom, a halogen atom, an optionally halogenated alkyl group having 1 to 4 carbon atoms, and $R^6$ and $R^8$ may bond to each other to form a ring system; in general formula (III), the bond between E' and G' is a double bond; E' represents a carbon atom; G' represents a carbon, oxy-gen, or nitrogen atom; the ring containing E' and G' represents a five-membered ring optionally containing (a) heteroatom(s), a six-membered ring containing (a) heteroatom(s), or a benzene, naphthalene, quinoline, isoquinoline, anthracene, or anthraquinone ring, and said ring containing E' and G' may be substituted with a hydroxyl group, a halogen atom, a nitro group, a cyano group, an alkyl group, or an alkoxy group; in general formula (IV), $R^9$ to $R^{17}$ each represent a hydrogen atom, or an optionally halogenated alkyl group having 1 to 4 carbon atoms in which (a) methylene group(s) in the chain may be replaced by $^\sim O^\sim$ or $^\sim CO^\sim$; M represents Fe, Co, Ni, Ti, Cu, Zn, Zr, Cr, Mo, Os, Mn, Ru, Sn, Pd, Rh, or Pt; and J represents a direct bond or an alkylene group having 1 to 8 carbon atoms in which (a) methylene group(s) may be replaced by $^\sim O^\sim$, $^\sim S^\sim$, $^\sim CO^\sim$, $^\sim COO^\sim$, $^\sim OCO^\sim$, $^\sim SO_2^\sim$, $^\sim NH^\sim$, $^\sim CONH^\sim$, $^\sim NHCO^\sim$, $^\sim N{=}CH^\sim$, or $-CH{=}CH^\sim$.

2. The optical recording medium according to claim 1, wherein $An^{m-}$ in general formula (I) is an anion other than perchlorate.

3. The optical recording medium according to claim 2, wherein at least one of $R^1$ and $R^2$ in general formula (I) is a benzyl group optionally substituted with a hydroxyl group, a halogen atom, a nitro group, a cyano group, an alkyl group, or an alkoxy group.

4. The optical recording medium according to claim 2, wherein X in general formula (I) is $CR^3R^4$.

5. The optical recording medium according to claim 2, wherein M is Fe and J is an alkylene group having 1 to 8 carbon atoms in general formula (IV).

6. The optical recording medium according to claim 1, wherein at least one of $R^1$ and $R^2$ in general formula (I) is a benzyl group optionally substituted with a hydroxyl group, a halogen atom, a nitro group, a cyano group, an alkyl group, or an alkoxy group.

7. The optical recording medium according to claim 6, wherein X in general formula (I) is $CR^3R^4$.

8. The optical recording medium according to claim 6, wherein M is Fe and J is an alkylene group having 1 to 8 carbon atoms in general formula (IV).

9. The optical recording medium according to claim 1, wherein X in general formula (I) is $CR^3R^4$.

10. The optical recording medium according to claim 9, wherein M is Fe and J is an alkylene group having 1 to 8 carbon atoms in general formula (IV).

11. The optical recording medium according to claim 1, wherein M is Fe and J is an alkylene group having 1 to 8 carbon atoms in general formula (IV).

* * * * *